United States Patent [19]

Eilrich et al.

[11] Patent Number: 4,986,586

[45] Date of Patent: Jan. 22, 1991

[54] DEVICE FOR REMOVING SOFT CONTACT LENS

[76] Inventors: Dinah K. Eilrich; Calvin H. Eilrich, both of 11945 Fir Dr., Reno, Nev. 89506

[21] Appl. No.: 424,331

[22] Filed: Oct. 16, 1989

[51] Int. Cl.⁵ ................................................ A61F 9/00
[52] U.S. Cl. ..................................... 294/1.2; 294/99.2
[58] Field of Search ................. 294/1.2, 8.5, 11, 33, 294/99.2, 902; 128/303 R; 206/5.1; 351/160 R; 606/1, 107, 210

[56] References Cited

U.S. PATENT DOCUMENTS

| | | | |
|---|---|---|---|
| 420,125 | 1/1890 | Swain | 294/99.2 |
| 1,200,158 | 10/1916 | Barrett | 294/99.2 X |
| 3,293,958 | 12/1966 | Smith | 294/99.2 X |
| 3,818,784 | 6/1974 | McClure | 294/99.2 |
| 4,093,291 | 6/1978 | Schurgin | 294/1.2 |
| 4,126,345 | 11/1978 | List | 294/1.2 |
| 4,192,204 | 3/1980 | Feldman | 294/1.2 |
| 4,245,859 | 1/1981 | Rainin | 294/1.2 |
| 4,717,190 | 1/1988 | Witherspoon | 294/99.2 |
| 4,750,771 | 6/1988 | Emmett | 294/1.2 X |
| 4,877,280 | 10/1989 | Milano | 294/99.2 |

*Primary Examiner*—Johnny D. Cherry
*Attorney, Agent, or Firm*—Milton S. Gerstein

[57] ABSTRACT

A soft, contact-lens remover having a tweezer-like main portion having a pair of legs, each leg defining a free end. Each free end telescopingly-receives thereover a retaining sleeve. A pair of removable and adjustable lens-removers are provided, one for each free end of the pair of legs. Each lens-remover has an elongated reed-like member that is frictionally held between a respective free end of one of the pair of legs and its respective retaining sleeve. Each lens-remover has a soft tip at one end of the reed-like member, which soft tips contact and remove a soft contact-lens from an eye. Each lens-remover is relatively positionable with respect to a free end of a leg both in the longitudinal, length-wise direction in order to adjust the projection of the soft tip, and also in the angular direction.

4 Claims, 1 Drawing Sheet

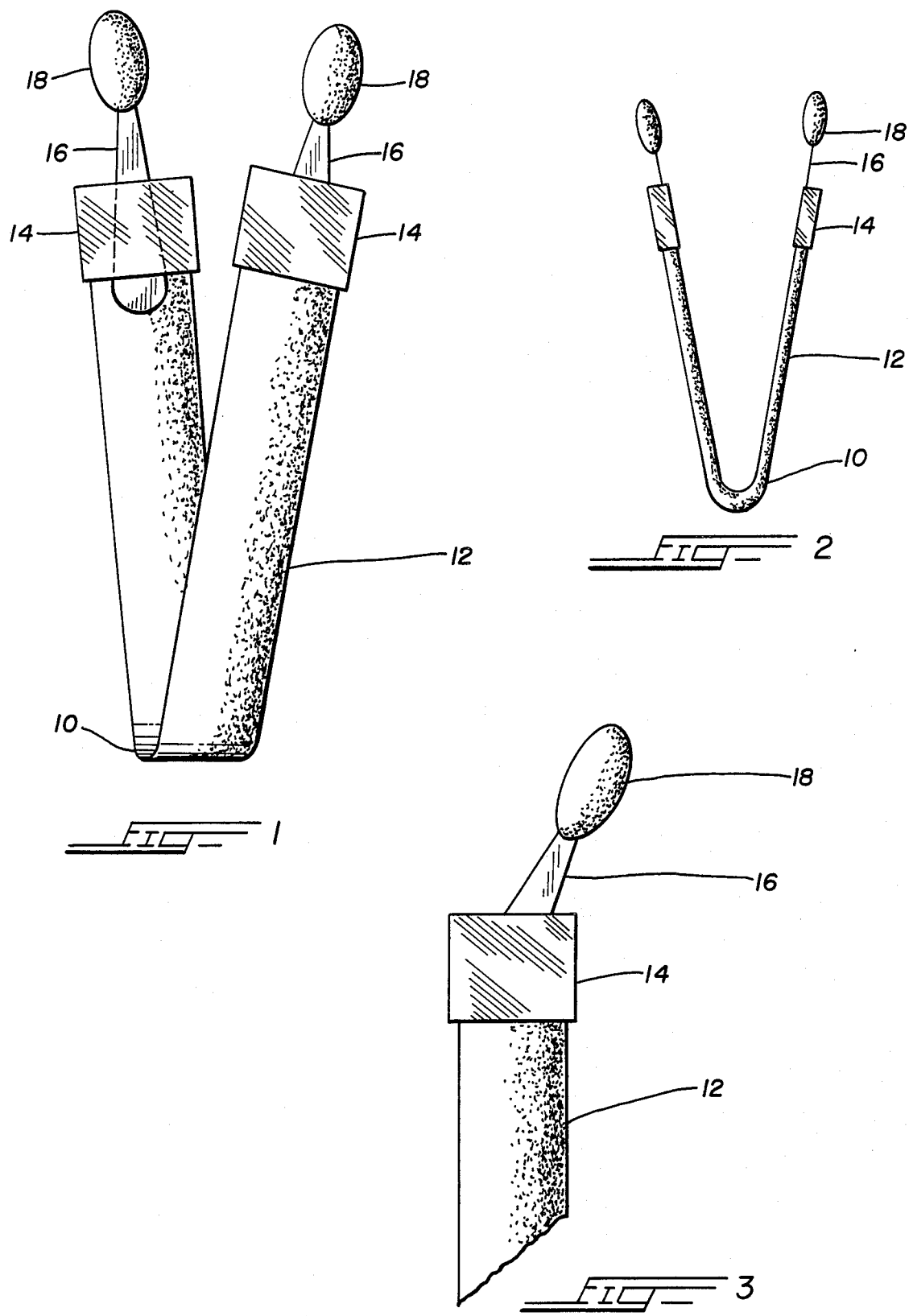

DEVICE FOR REMOVING SOFT CONTACT LENS

BACKGROUND OF THE INVENTION

This invention relates to contact lens, specifically, the removal of soft contact lens from an eye, offering a more sanitary and safe alternative to using fingers.

SUMMARY OF THE INVENTION

Accordingly, several objects and advantages of our invention are described below.
- (a) To provide a more sanitary, a more convenient, and safer alternative to using fingers.
- (b) To provide an inexpensive, affordable device that can be purchased by the general public.
- (c) To provide a light weight, small, slim size makes it a convenient hand held device.
- (d) The soft tipped end of the device will provide for easier gripping of the soft contact lens.
- (e) To provide a device that can be used by persons of all ages.
- (f) Made of sturdy, durable ABS plastic that has a non slippery surface.
- (g) It will have a U-shape for an easier hand held grip.
- (h) To provide a device for persons, namely women with long finger nails that find it difficult to remove their soft contact lens from their eyes. To avoid injury to either eye or soft contact lens.
- (i) To provide a device that will aid persons afflicted with arthritis in the hand or finger joints or both.
- (j) To provide a device that will make the removal of soft contact lens easier, safer and more convenient because of the controversy regarding the damage or disease the eye can receive if soft contact lens, regardless if they're daily wear or extended wear, are not removed every night, and not cleaned properly.
- (k) To provide a device for persons that don't like to put their fingers in their eyes, or have rough, or dirty hands or fingers.

Further objects and advantages of our invention will become apparent from a consideration of the ensuing description and drawings.

BRIEF DESCRIPTION OF DRAWINGS

FIG. 1 is perspective view of the invention and showing the adjustable soft tipped applicator thereof;

FIG. 2 is a side view thereof;

FIG. 3 is a detail view showing the soft tipped end angled for better gripping of the soft contact lens.

DETAILED DESCRIPTION OF THE INVENTION

The body or base of the contact removal device 10 is made of ABS plastic with a slightly rigid surface on the outer part of the device, while the inside has a smooth finish. The slightly rigid surface on the outside will provide a nonslippery, easier to grip base.

By starting with an oblate piece of ABS plastic it is cut ¼" wide and 5½" in length. Laying down flat, it is then heat bent in the middle, and bent over until it reaches an approx. ¾" width between ends, thus forming a U-shape member. The base of the device after being heat bent will now be approx. ¼" wide by 2¾" in length, in its synclinal form. At the free ends of the legs 12 is one section 14 each of #9 clear vinyl tubing 7/16" OD, cut into ¼" lengths, stretched over the ends, pushed down to be even with the tip of the U-shaped member.

FIGS. 1 and 2 show a one-piece soft tipped applicator 18 on a thin colored plastic handle or elongated reed-like member that is inserted between the free end of a leg 12 and the clear vinyl tubing 14, inserting it far enough down to where it is to a convenient length, and angle.

The manner of using the invention is similar to the opening and closing motion of tweezers. By holding the device in either hand, the thumb and the fore finger will rest on the clear vinyl tubings 14. One brings the device up to the eye needing the contact lens taken out, puts gentle pressure on the contact lens with the soft tips 18, squeezes the device together in a tweezer motion, gripping the contact lens and gently pulling away from the eye, thus removing the contact lens. The longitudinal and angular adjustability of the tips 18 provide for easier and safer use.

We claim:

1. In a soft contact-lens aid device having a first and a second leg, each said leg having a first end and a second end, and a base at which said first ends are interconnected for providing a tweezer-like member, a first and second contact lens remover associated with said second ends of said legs, one said remover for one said second end, wherein the improvement comprises:
    first and second mounting means for respectively mounting said first and second removers to a respective said second end of said legs, each said mounting means comprising means for adjustably positioning the respective said remover with respect to the respective said second end;
    each said means for adjustably positioning allowing for the respective said remover to be adjusted with respect to the associated said second end both in a longitudinal, lengthwise direction and in an angular direction, said longitudinal direction being taken parallel to the length of the respective said leg;
    each said means for adjustably positioning comprising a sleeve member telescopingly, slidingly received over said second end of a respective said leg for free movement therealong; each said remover comprising an elongated main body element having a first end portion and a second end portion, and a soft-tip means at said second end portion of said elongated main body element for contacting a soft contact lens in an eye for effecting removal thereby; said first end portion of said elongated main body element being received between said second end of a respective said leg and said sleeve member, whereby the remover is frictionally held therebetween in a desired, adjusted-to position, said adjustment being accomplished by the location of said first end portion of said elongated main body element of the remover between the respective said sleeve member and second end of the leg.

2. The improvement according to claim 1, wherein said elongated main body element has a width along the entire length thereof less than the width of said sleeve member, whereby said angular adjustable positioning of said remover may be accomplished.

3. The improvement according to claim 1, wherein the length of said elongated main body element is greater than the length of said sleeve member.

4. The improvement according to claim 1, wherein said sleeve member defines an interior hollow volume having a thickness greater than the thickness of a respective said second end of a respective said leg, whereby said sleeve member may slide along said second end of said leg and receive said elongated main body element therethrough.

* * * * *